US00PP20869P2

(12) United States Plant Patent
Shackelford

(10) Patent No.: US PP20,869 P2
(45) Date of Patent: Mar. 23, 2010

(54) ***ILEX* PLANT NAMED 'SHACKELFORD'**

(50) Latin Name: *Ilex vomitoria*
Varietal Denomination: Shackelford

(76) Inventor: David T. Shackelford, P.O. Box 167, West Columbia, TX (US) 77486

( * ) Notice: Subject to any disclaimer, the term of this patent is extended or adjusted under 35 U.S.C. 154(b) by 0 days.

(21) Appl. No.: 12/380,505

(22) Filed: Feb. 27, 2009

(51) Int. Cl.
*A01H 5/00* (2006.01)

(52) U.S. Cl. ..... Plt./247
(58) Field of Classification Search ..... Plt./247
See application file for complete search history.

*Primary Examiner*—Annette H Para
(74) *Attorney, Agent, or Firm*—Penny J Aguirre

(57) ABSTRACT

A new cultivar of *Ilex vomitoria*, 'Shackelford', characterized by its glossy, small sized leaves that are bright yellow in color throughout the year with new growth that is rose red in color, its dense, low growing evergreen growth habit that lends itself to a variety of landscape sites, and its cold hardiness to U.S.D.A. Zone 7.

1 Drawing Sheet

Botanical classification: *Ilex vomitoria.*
Variety denomination: 'Shackelford'.

BACKGROUND OF THE INVENTION

The present invention relates to a new and distinct cultivar of *Ilex vomitoria* and will be referred to hereafter by its cultivar name, 'Shackelford'. 'Shackelford' is a new cultivar of Yaupon holly grown for use as a landscape plant.

The Inventor discovered 'Shackelford' in his nursery in the spring 1998 in West Columbia, Tex. The new cultivar arose as a naturally occurring branch mutation found on a plant *Ilex vomitora* 'Shillings' (not patented) growing in a container amongst a large block of nursery stock.

Asexual reproduction of the new cultivar was first accomplished by the Inventor using semi-hardwood stem cuttings in 1998 in West Columbia, Tex. The characteristics of 'Shackelford' have been determined to be stable and are reproduced true to type in successive generations.

SUMMARY OF THE INVENTION

The following traits have been observed repeatedly and represent the characteristics of the new cultivar as grown outdoors in trial beds and in containers in West Columbia, Tex. These attributes in combination distinguish 'Shackelford' as a unique cultivar of *Ilex.*

1. 'Shackelford' exhibits foliage that is bright yellow in color with the coloration remaining yellow throughout the year.
2. 'Shackelford' exhibits leaves that are glossy and small in size.
3. 'Shackelford' exhibits new foliage growth that is rose red in color.
4. 'Shackelford' forms a dense, low growing, evergreen mound that can be used in a wide variety of landscape situations.
5. 'Shackelford' is hardy to U.S.D.A. Zone 7.

'Shackelford' is unique for its yellow colored foliage, a characteristic that is not found on any species or cultivars of *Ilex vomitoria* known to the Inventor. 'Shackelford' is similar to the parent plant, 'Schillings', in plant habit and in having small sized leaves, however 'Schillings' differs from 'Shackelford' in having green foliage. Plants of the species, *Ilex vomitoria*, differ from 'Shackelford' in having larger sized leaves that are green in color.

BRIEF DESCRIPTION OF THE DRAWING

The accompanying colored photographs illustrate the overall appearance and distinct characteristics of 6 year-old plants of the new *Ilex* as grown outdoors in 36-gallon containers in West Columbia, Tex. in 2008.

The photograph in FIG. 1 illustrates the overall appearance of 'Shackelford'.

Figure 1:
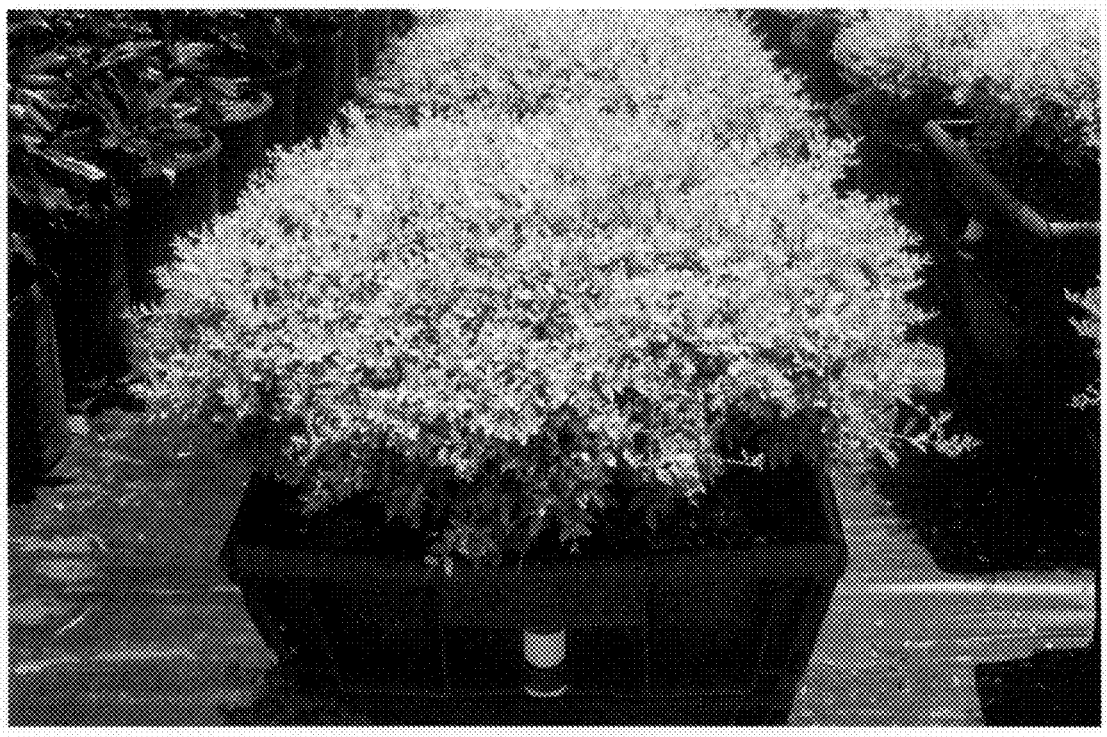
Figure 2:
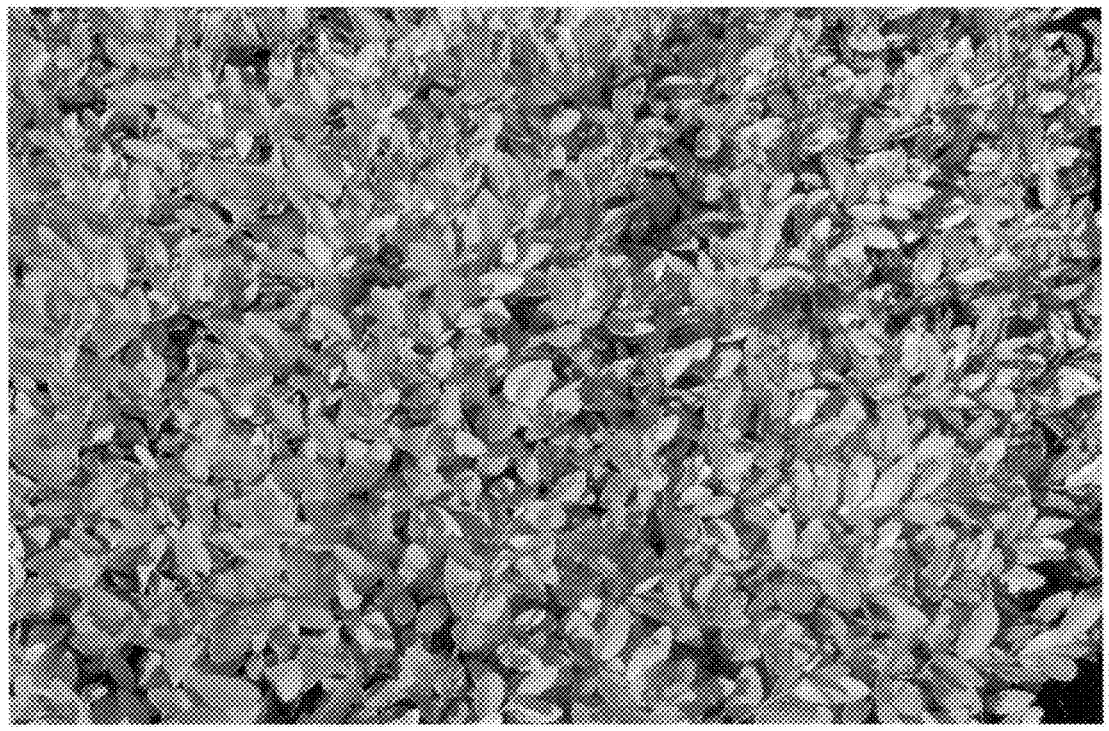

The photograph in FIG. 2 is a close-up view of the foliage and illustrates the coloration of the mature and emerging leaves of 'Shackelford'.

The colors in the photograph may differ slightly from the color values cited in the detailed botanical description, which accurately describe the colors of the new *Ilex.*

DETAILED BOTANICAL DESCRIPTION

The following is a detailed description of 6 year-old plants of the new cultivar as grown outdoors in 36-gallon containers in West Columbia, Tex. The phenotype of the new cultivar may vary with variations in environmental, climatic, and cultural conditions, as it has not been tested under all possible environmental conditions. The color determination is in accordance with the 2001 R.H.S. Colour Chart of The Royal Horticultural Society, London, England, except where general color terms of ordinary dictionary significance are used.

General description:

*Flowering period.*—No flowers observed.
*Plant type.*—Evergreen, perennial shrub.
*Plant habit.*—Dense, low growing, mounding.
*Height and spread.*—Reaches about 28 cm in height and 45.5 cm in width as grown in a 36 gallon container.
*Hardiness Zone.*—U.S.D.A Zone 7.
*Diseases resistance.*—No susceptibility or resistance to diseases or pests has been observed.
*Root description.*—Fibrous.
*Propagation.*—Semi-hardwood stem cuttings.
*Growth rate.*—Slow to moderate.

Stem description:

*Shape.*—Round.

*Stem color.*—New growth 179C with tips 178A, mature wood 199A to 199B.

*Stem size.*—Main stems; average of 4.4 cm in diameter, lateral branches; average 38 cm in length and 1 cm in width, secondary lateral branches; average of 22 cm in length and 0.5 cm in width.

*Stem surface.*—Glabrous on new growth, becoming woody with smooth bark with fissures.

*Internode length.*—Lateral branches; an average of 1.5 cm.

*Branching.*—Densely branched; 4 to 5 main branches, with numerous secondary branches, branches are formed freely if pinched.

Foliage description:

*Leaf shape.*—Oval to Elliptic.

*Leaf division.*—Simple.

*Leaf base.*—Cuneate.

*Leaf apex.*—Obtuse.

*Leaf fragrance.*—None.

*Leaf venation.*—Even-pinnate, midrib is impressed on upper surface and prominent on lower surface, 12D to 144C in color, all other veins match leaf color.

*Leaf margins.*—Crenate.

*Leaf arrangement.*—Alternate.

*Leaf aspect.*—Held horizontal.

*Leaf attachment.*—Petiolate.

*Leaf surface.*—Glabrous, glossy on upper surface, dull on lower surface.

*Leaf size.*—Average of 2.2 cm in length and 1 cm in width when mature.

*Leaf quantity.*—Numerous, average of 25 per stem that is 13 cm in length.

*Leaf internode length.*—Average of 0.5 cm.

*Leaf color.*—Newly expanding leaves; 178A on upper and lower surface, mature leaves; 12A to 12B with older shaded leaves 137B on upper surface and 12C with older shaded leaves 144C on lower surface.

*Petioles.*—An average of 2.75 mm in length and 1 mm in width, held at about a 45° angle, 137B in color, glabrous surface.

*Stipels and stipules.*—Not present.

Flower description: No blooms or berries have been observed on the new cultivar.

It is claimed:

1. A new and distinct cultivar of *Ilex* plant named 'Shackelford' as herein illustrated and described.

* * * * *